United States Patent
Dreiling et al.

(10) Patent No.: US 7,475,601 B2
(45) Date of Patent: Jan. 13, 2009

(54) TUFT GRIPPING STRENGTH TEST FOR PRIMARY BACKING MAT AND METHOD

(75) Inventors: Cari Ann Dreiling, Ft. Lupton, CO (US); Lester M. Aseere, Parker, CO (US)

(73) Assignee: Johns Manville, Denver, CO (US)

( * ) Notice: Subject to any disclaimer, the term of this patent is extended or adjusted under 35 U.S.C. 154(b) by 272 days.

(21) Appl. No.: 11/304,050

(22) Filed: Dec. 15, 2005

(65) Prior Publication Data

US 2007/0137294 A1  Jun. 21, 2007

(51) Int. Cl.
*G01N 3/08* (2006.01)
(52) U.S. Cl. ....................................................... 73/827
(58) Field of Classification Search .................. None
See application file for complete search history.

(56) References Cited

U.S. PATENT DOCUMENTS

| | | | | | |
|---|---|---|---|---|---|
| 2,588,130 | A | * | 3/1952 | Lemon et al. | 156/72 |
| 4,654,247 | A | * | 3/1987 | Randall et al. | 428/95 |
| 5,605,108 | A | * | 2/1997 | Woosley | 112/475.23 |
| 2006/0013989 | A1 | * | 1/2006 | Stull et al. | 428/95 |

OTHER PUBLICATIONS

Lloyd Instruments, "TG 5012", copyright 2002.*

* cited by examiner

*Primary Examiner*—Robert R Raevis
(74) *Attorney, Agent, or Firm*—Robert D. Touslee

(57) ABSTRACT

A test method for measuring tuft gripping strength characteristics of a tufted nonwoven primary backing mat for making tufted carpets, the tufted backing mat having no additional binder on the backside of the mat for tufted carpet is disclosed. The test is used in a method of developing primary backing mats for making tufted carpets that are competitive or superior in TGS.

12 Claims, No Drawings

TUFT GRIPPING STRENGTH TEST FOR PRIMARY BACKING MAT AND METHOD

The invention involves a test method for determining the capability of primary backing mats to grip tufts of yarn before any additional adhesive or binder is applied to the backside of the tufted interim product, and a method of using the test in making a suitable primary backing mat for tufted carpet, using the test method to determine the gripping strength of mats that are currently being used and candidate mats.

BACKGROUND

In the manufacture of tufted carpet a fibrous nonwoven or woven primary mat, such as a spunbonded mat more than 2-4 meters wide is run through a tufting machine and tufted. Normally, this produces a tufted interim product that is rolled up and put into storage until an order for that type and color of tufted carpet is received by the carpet line. The tufts are held in the primary backing only by the friction of the primary backing mat on the strands of yarn penetrating the mat. At that time the roll of tufted interim product is removed and installed on the carpet line where all or a portion of the roll of interim product is finished into a carpet including applying a binder or adhesive to the backside of the primary mat to lock the tufts into position on the primary backing. Often the entire roll of interim product is not used for the order and the unused portion, smaller roll, is removed and put back into storage. A problem the carpet industry has in handling the rolls of tufted interim products is that sometimes one or more tufts is contacted by something on the production line or in transit to and from storage that pulls out one or more tufts and ruins the roll, or at least a section of the roll of interim product, a costly problem. This also happens in the tufting process. This happens with some primary backing mats more than others, but the reason why has not been known. In the past there has been no way to measure how difficult it is to pull out tufting from the interim tufted products. The characteristic of the primary backing mat for holding tufts prior to the application of binder or adhesive and curing is very important and is not constant for all primary backing mats.

Tests do exist for measuring the Tuft Withdrawal Force or Grab Strength for finished tufted carpet products, such as ASTM D-1335 or AWTA Test Code T-34, but in the finished carpet the magnitude of force required to remove a tuft is magnitudes higher and is done for a totally different reason, i.e. to determine how well the carpet will resist vacuum cleaners and wear and tear that tends to pull on the tufts. A test for an interim tufted product, and the use of such a test to improve the characteristics of the primary backing for holding tufts in place has not been developed.

SUMMARY

The invention includes an embodiment comprising tufting a primary backing mat by using a taller loop height and wider tufting needle spacing than is normally used in making a normal interim tufted product to produce an interim tufted test product having no additional binder or adhesive on the backside of the test product, selecting one loop of the tufting on the top of the interim tufted test product, severing the tops of each loop adjacent the selected loop, contacting the selected loop at its top and pulling that loop from the primary backing while measuring the magnitude of force required to remove the loop, thereby determining Tuft Gripping Strength, TGS, for the primary backing mat. By "at the top" as it refers to the tuft being tested is meant at or close to the center of the tuft, i.e. +/−1 mm from the center of the loop. It is more typical to sever or cut each adjacent loop at the top of the loop before pulling the selected loop from the primary backing to reduce TGS variability, i.e. when the adjacent loops are not severed at their top, the data is much more variable and not as indicative of the TGS.

By TGS is meant the maximum force required to pull a loop from the primary backing of the tufted interim test product. By a wider needle spacing is meant using fewer needles in a needle bar that is used in making an interim tufted product for a carpet and more typically every other needle, or more, is removed before tufting the primary backing mat for testing. This makes the stitch rows farther apart Also, the loops on the topside are made larger, higher, and typically are about 7.8 mm for convenience of the test, but can be the same as in the actual interim tufted products or can be larger, even larger than 12 mm. The loops on the backside of the interim tufted test product are normal for the tuft in use. The typical Gripping Strength of spunbonded polyester primary backing mats is less than one pound of force, such as in a range of about 0.2 to about 0.8 lbs., but with this invention it will now be possible to develop primary backings having even higher Tuft Gripping Strengths.

The invention also includes an embodiment comprising producing two or more primary backing mats having different characteristics, tufting each of the primary backing mats by using a wider tufting needle spacing than is used in making an interim tufted product to produce an interim tufted test product having no significant amount of binder or adhesive on the backside of the test product, selecting one loop of the tufting on the top of the interim tufted test product, contacting the selected loop at the top and pulling that loop from the primary backing while measuring the magnitude of force required to remove the loop thereby determining Tuft Gripping Strength, TGS, for each of the primary backing mats and selecting the primary backing mat having the highest TGS for a primary backing mat for use in making tufted carpets.

A first competitor's spunbonded polyester primary backing mat was tufted in the manner described above and ten samples of the mat was then tested for TGS in the manner described above. This first competitor's product had an average TGS of 0.782 lb. This procedure was repeated with a second competitors spunbonded primary backing mat and it had an average TGS of 0.641 lb. A first candidate spunbonded polyester mat was tufted in the same manner and tested in the same manner, resulting in an average TGS of 0.667 lb. Because of the invention, it was then possible to determine that this first candidate was inferior in TGS to one of the competitive products, a fact that in the past would not have been learned until a customer had experienced many tuft pull out problems and lost substantial interim product at substantial cost. Knowing this prior to sampling a customer with the first candidate product, further modifications were made to the mat resulting in a much improved polyester spunbonded mat that when tufted in the same manner and tested in the same manner showed an average TGS of 0.839 lb. By going to the customer(s) with this mat, there is a much larger chance of approval and good sales of the primary backing mat than by sampling the customer with what appeared to be the best mat candidate, before this test was available.

Different embodiments employing the concept and teachings of the invention will be apparent and obvious to those of ordinary skill in this art and these embodiments are likewise intended to be within the scope of the claims. The inventor does not intend to abandon any disclosed inventions that are reasonably disclosed but do not appear to be literally claimed below, but rather intends those embodiments to be included in the broad claims either literally or as equivalents to the embodiments that are literally included.

The invention claimed is:

1. A method of determining the capability of a primary backing mat to grip tufts of yarn in a tufted interim product containing the primary backing mat and before any adhesive or binder has been applied to the tufted interim product comprising, tufting a sample of the primary backing mat using a wider tufting needle spacing than is used in making the tufted interim product to produce a tufted test sample containing the primary backing mat and having no adhesive or binder applied after tufting, selecting a loop in the test sample for testing, severing the top of each loop adjacent the selected loop, gripping the selected loop at its top and pulling at least one part of the selected loop out of the tufted test sample and recording the magnitude of force required to pull the at least one part of the selected loop out of the tufted test sample.

2. The method of claim 1 wherein the primary backing mat is a spunbonded mat.

3. The method of claim 1 wherein the tufting done using a wider tufting needle spacing than is used in making the tufted interim product is accomplished by removing every other needle from a needle bar used to make the tufts, loops in the tufted interim product prior to tufting the primary backing mat using the needle bar to make said tufted test sample.

4. The method of claim 3 wherein the primary backing mat is a spunbonded mat.

5. The method of claim 3 wherein the loops in said tufted test sample are made taller than the loops in said tufted interim product.

6. The method of claim 1 wherein the loops in said tufted test sample are made taller than the loops in said tufted interim product.

7. A method of making a primary backing mat suitable for making tufted carpet comprising laying down a web of fibers and bonding the fibers together to form a primary backing mat for tufted carpet, the improvement comprising tufting a sample of the primary backing mat using a wider needle spacing than is ordinarily used to produce a tufted interim product to make a tufted TGS test sample having no adhesive or binder applied after tufting, selecting a loop in the tufted TGS test sample for testing, severing the top of each loop adjacent the selected loop, gripping the selected loop at its top and pulling at least one part of the loop out of the tufted TGS test sample, recording the highest magnitude of force required to pull at least one part of the loop out of the tufted TGS test sample.

8. The method of claim 7 wherein one or more primary backing mat parameters are modified to achieve a higher TGS, the modified primary backing mat is tufted to produce a tufted TGS test sample and the tufted TGS sample is tested to obtain the TGS of the modified primary backing mat.

9. The method of claim 7 wherein the tufting is done using a wider tufting needle spacing by removing every other needle from a needle bar used to make the loops in the tufted interim product and using the needle bar containing fewer needles to tuft the primary backing mat to make the tufted TGS test sample.

10. The method of claim 9 wherein one or more primary backing mat parameters are modified to achieve a higher TGS, the modified primary backing mat is tufted to produce a tufted TGS test sample and the tufted TGS sample is tested to obtain the TGS of the modified primary backing mat.

11. The method of claim 10 wherein the primary backing mat is a spunbonded mat.

12. The method of claim 7 wherein the primary backing mat is a spunbonded mat.

* * * * *